United States Patent [19]
Cohen et al.

[11] Patent Number: 5,458,606
[45] Date of Patent: Oct. 17, 1995

[54] NEURO ENDOSCOPE FOR SHUNT

[75] Inventors: Donald Cohen, Irvine; Lance Kumm, Tustin; John Aoki, Bellflower; Rith N. Kimm, Rancho Santa Margarita; Shea Bassett, Newport Beach, all of Calif.

[73] Assignee: Neuro Navigational Corporation, Costa Mesa, Calif.

[21] Appl. No.: 307,503

[22] Filed: Sep. 16, 1994

Related U.S. Application Data

[62] Division of Ser. No. 285,487, Aug. 3, 1994, which is a continuation of Ser. No. 53,075, Apr. 26, 1993, abandoned, which is a continuation-in-part of Ser. No. 970,402, Nov. 2, 1992, abandoned.

[51] Int. Cl.⁶ ............................................. A61B 1/00
[52] U.S. Cl. .................. 606/108; 604/8; 606/16; 600/109
[58] Field of Search .................. 606/1, 108, 15, 606/16, 2; 604/8, 164, 264, 284, 317; 607/1; 128/6, 4

[56] References Cited

U.S. PATENT DOCUMENTS

| | | | |
|---|---|---|---|
| 2,621,651 | 12/1952 | Wallace | 128/4 |
| 3,020,913 | 2/1962 | Heyer | 128/350 |
| 4,023,559 | 5/1977 | Gaskell | 128/2 |
| 4,562,838 | 1/1986 | Walker | 128/303.14 |
| 4,586,491 | 5/1986 | Carpenter | 128/6 |
| 4,623,789 | 11/1986 | Ikeda et al. | 250/227 |
| 4,624,243 | 11/1986 | Lowery et al. | 128/6 |
| 4,681,104 | 7/1987 | Edelman | 606/7 |
| 4,682,596 | 7/1987 | Bales et al. | 128/303.14 |
| 4,758,222 | 7/1988 | McCoy | 128/6 X |
| 4,770,653 | 9/1988 | Shturman | 606/7 |
| 4,782,819 | 11/1988 | Adair | 606/15 |
| 4,785,815 | 11/1988 | Cohen | 606/7 |
| 4,785,815 | 11/1988 | Cohen | 606/7 |
| 4,791,926 | 12/1988 | Fry | 606/15 |
| 4,998,527 | 3/1991 | Meyer | 128/4 |
| 5,021,059 | 6/1991 | Kensey et al. | 606/213 |
| 5,041,108 | 8/1991 | Fox et al. | 606/7 |
| 5,057,107 | 10/1991 | Parins et al. | 606/48 |
| 5,084,045 | 1/1992 | Helnowski | 606/32 |
| 5,152,277 | 10/1992 | Honda et al. | 128/4 |
| 5,159,920 | 11/1992 | Condon et al. | 128/6 |
| 5,207,684 | 5/1993 | Nobles | 606/108 |
| 5,370,640 | 12/1994 | Kolff | 606/2 |
| 5,385,541 | 1/1995 | Kirsch et al. | 604/8 |

Primary Examiner—Stephen C. Pellegrino
Assistant Examiner—Glenn Dawson
Attorney, Agent, or Firm—John L. Rogitz

[57] ABSTRACT

A shunt for relieving hydrocephalus has a closed distal end and an aperture formed in the distal end. A hollow hypotube has a distal end, and the hypotube holds an image fiber which protrudes beyond the distal end of the hypotube. The hypotube is positioned in the shunt with the distal end of the hypotube abutting the distal end of the shunt and the image fiber protruding through the aperture. The hypotube with shunt can then be advanced into the brain of a patient, while the surgeon views the path of advancement on a nearby video monitor which is connected to the image fiber. In an alternate embodiment, the distal end of the image fiber is flush with the distal end of the hypotube. The shunt has a slit formed in its distal end, and the hypotube with image fiber can be selectively advanced through the slit to view the area of the brain beyond the catheter.

16 Claims, 4 Drawing Sheets

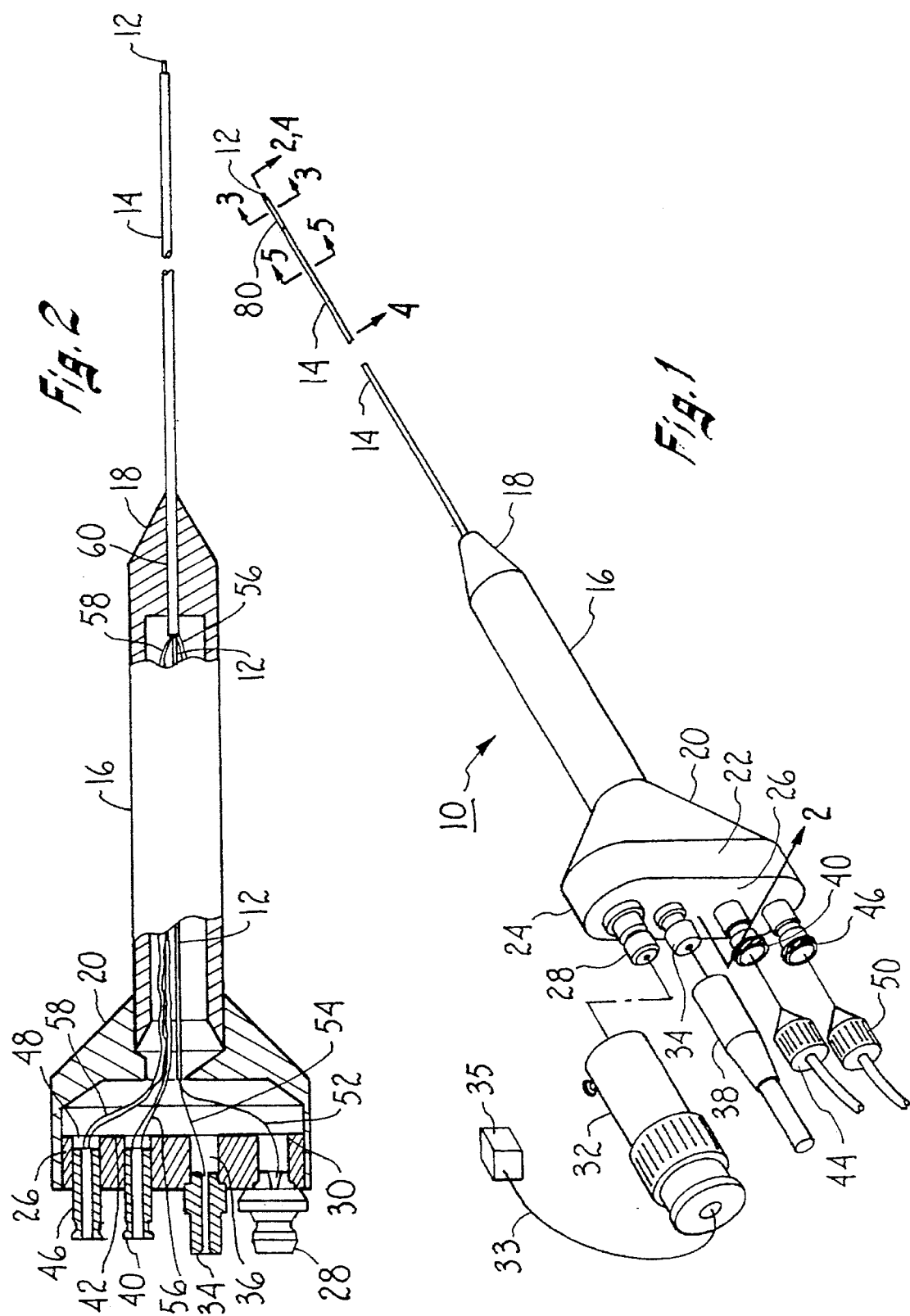

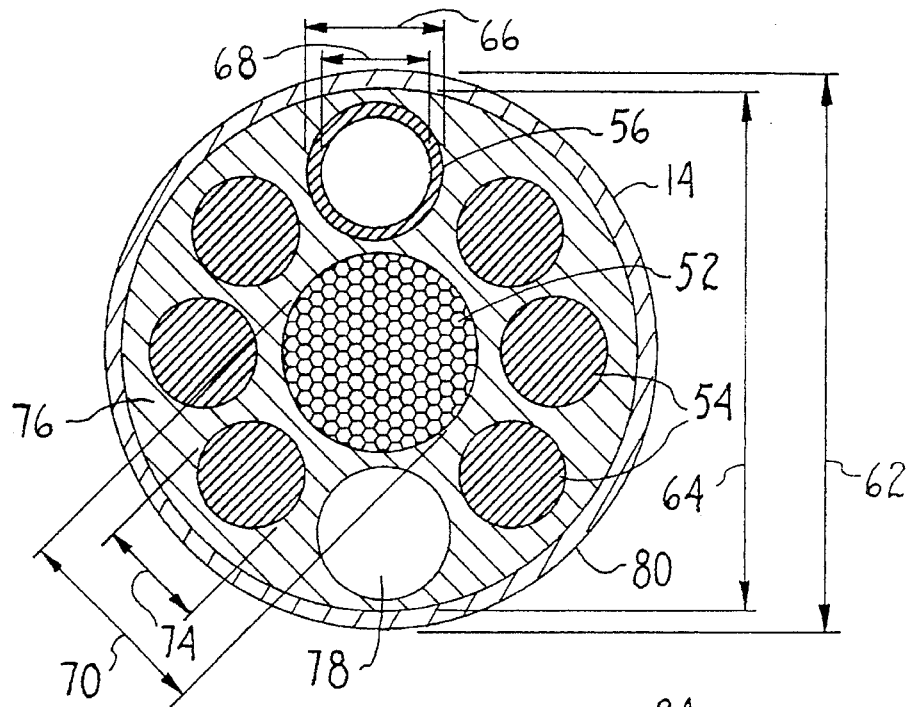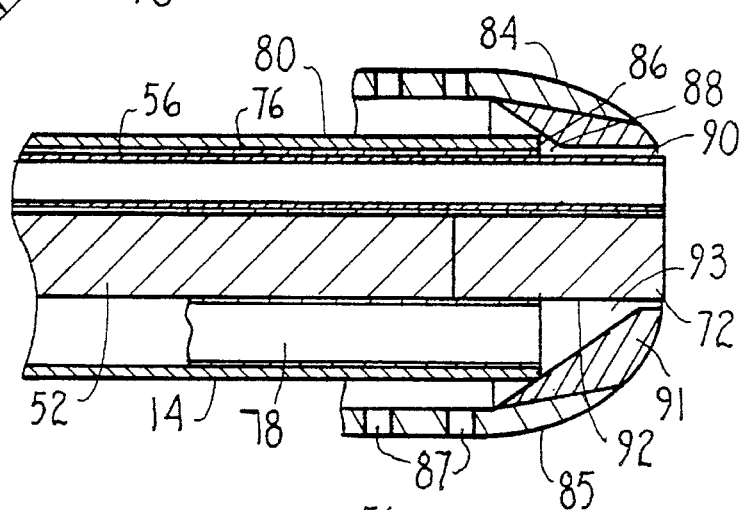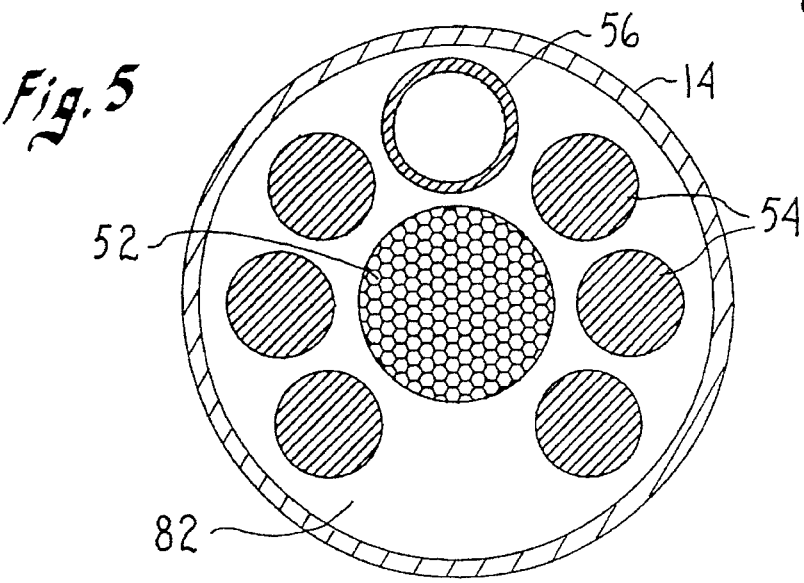

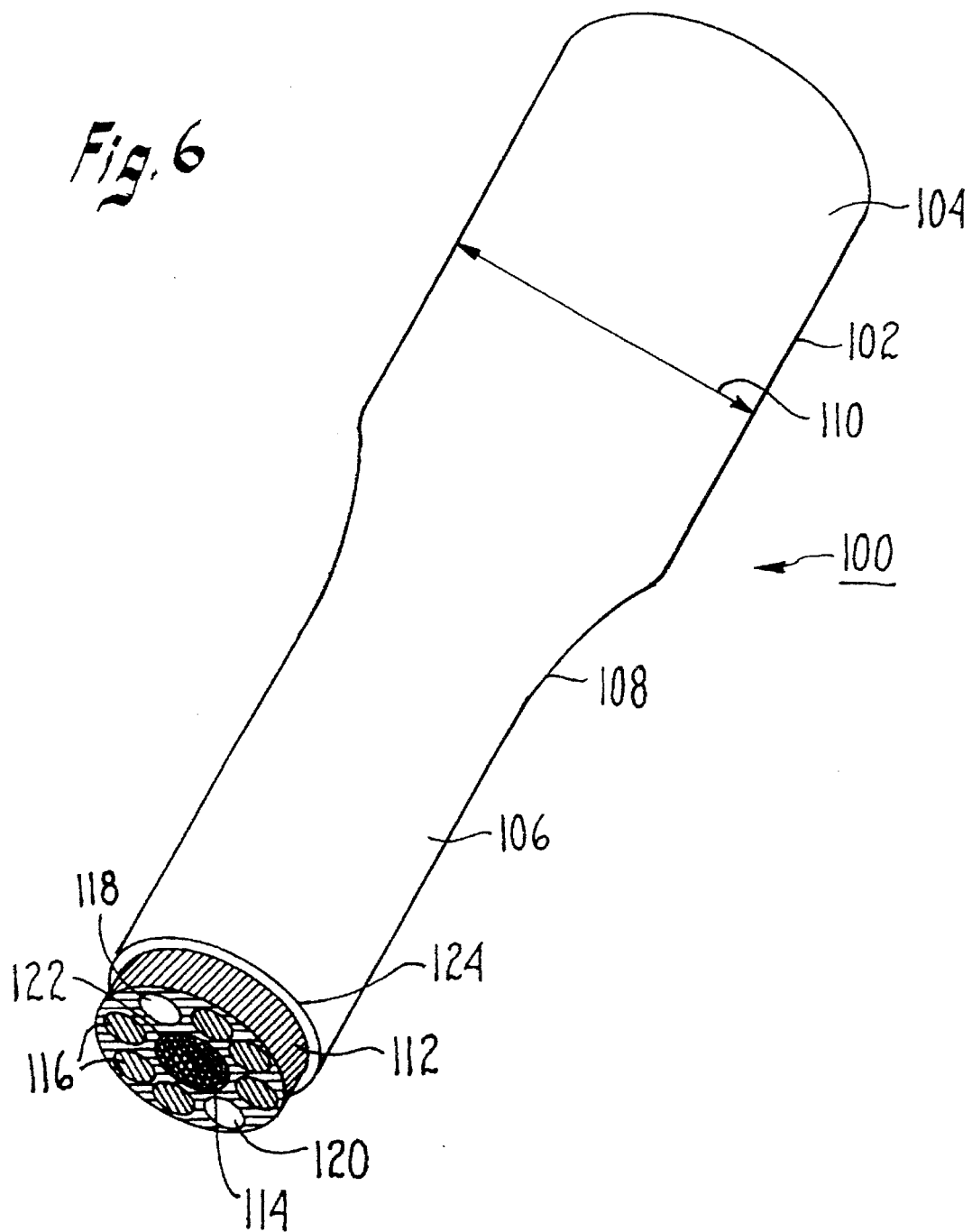

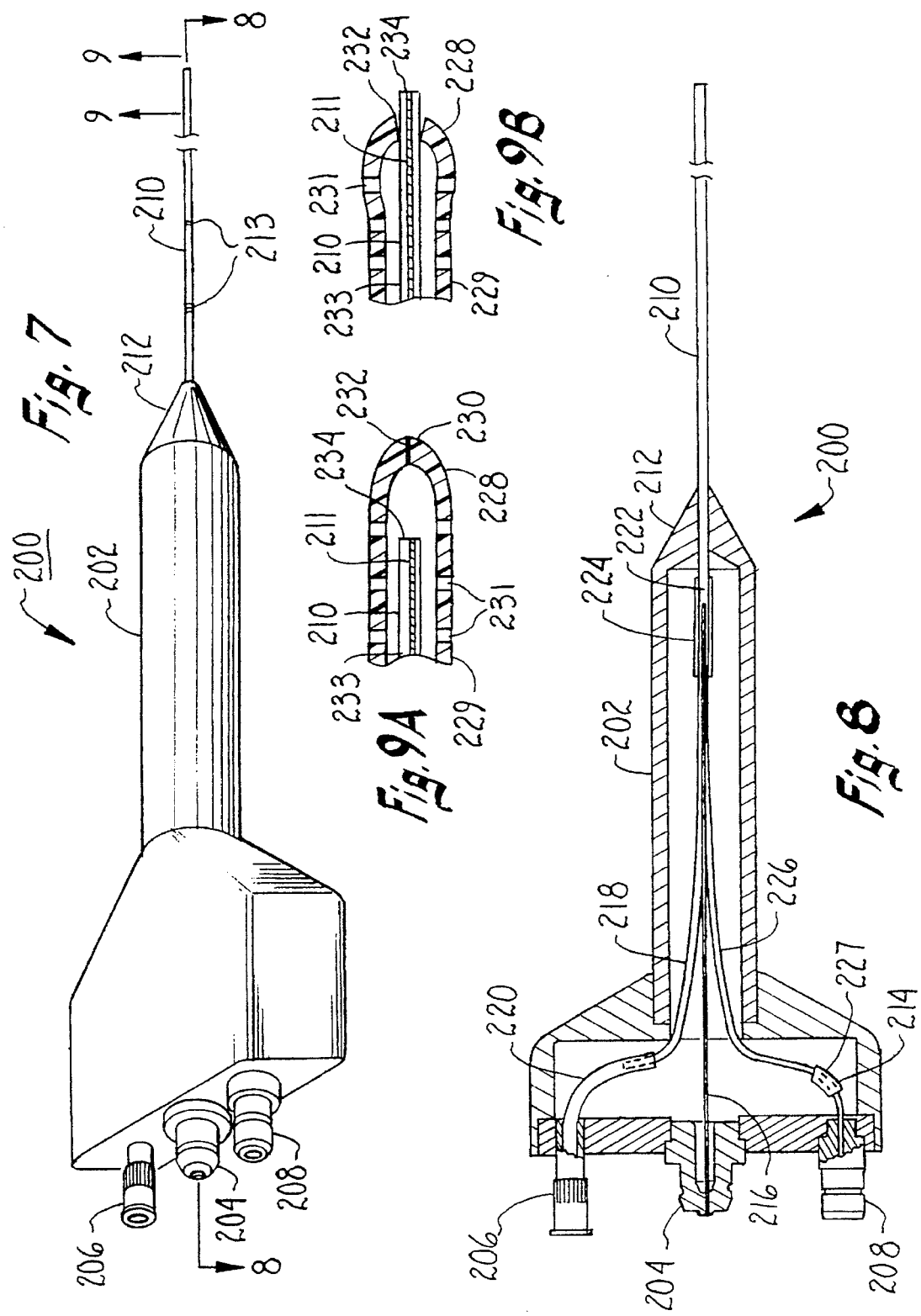

NEURO ENDOSCOPE FOR SHUNT

This application is a divisional of application Ser. No. 08/285,487, filed Aug. 3, 1994, now pending, which is a continuation of Ser. No. 08/053,075 filed Apr. 26, 1993, now abandoned.

FIELD OF THE INVENTION which is a continuation-in-part of and claims priority from co-pending U.S. patent application for an invention entitled "ENDOSCOPE FOR SHUNT PLACEMENT", assigned to the same assignee as the present invention, Ser. No. 07/970,402, filed Nov. 2, 1992, now abandoned, which application is fully incorporated herein by reference.

The present invention relates generally to neurosurgery instruments, and more particularly to devices for the in vivo placement of ventricular shunt catheters.

BACKGROUND

Hydrocephalus, familiarly known as water on the brain, is an affliction which affects many people, including children. One of the symptoms of this serious malady is increased fluid pressure on the brain of the victim, which, unless relieved, can result in excruciating pain, and can potentially cause brain damage to the victim.

Hydrocephalus causes a slow, continuous build-up of fluid pressure on the brain. More specifically, in a patient afflicted with hydrocephalus, excess body fluid (cerebral spinal fluid, or CSF) slowly and continuously accumulates in the ventricles of the brain. To extract the excess body fluid from in the ventricles of the brain and thereby relieve the fluid pressure on the brain, techniques, many of which are minimally-invasive, have been developed for establishing a pathway for fluid communication from the area of accumulated fluid to an area external to the cranial cavity.

As an example of one such minimally-invasive technique, a long, slender catheter known as a "shunt" is advanced through a small entry site in the skull of a patient who is afflicted with hydrocephalus, and a distal end segment of the shunt is positioned in one of the ventricles of the brain. The proximal end of the shunt is connected to a valve which regulates the flow of excess cerebral spinal fluid (CSF) out of the skull and into another body cavity, e.g., the peritoneum or venous system. In other words, the excess CSF in the skull is drained through the shunt, to permit the restoration of a normal pressure in the skull (i.e., to restore normal intercranial pressure).

Typically, a plurality of small holes are formed in the distal end segment of the shunt catheter, and fluid that accumulates in the ventricle enters the holes and drains through the shunt, thereby relieving the fluid pressure on the brain.

Unfortunately, the small holes in the distal end segment of the shunt can become clogged, thereby impeding the draining of excess fluid from the cranial cavity. More specifically, a portion of the brain known as the choroid plexus can grow into the holes of the distal end segment of the shunt and clog the holes. When this occurs, it is necessary to remove the shunt from the brain and replace the shunt with another unclogged shunt.

Accordingly, it is desirable to avoid positioning the shunt too near the choroid plexus, to avoid eventual clogging of the shunt. On the other hand, the holes of the shunt catheter must be positioned in a precise location (which varies depending upon the patient's condition) in the ventricle to ensure that the shunt will effectively drain excess CSF.

It is not simple, however, to precisely position the shunt so that it will effectively drain excess brain fluid, while remaining unclogged by the choroid plexus. This is largely because in most shunt placement procedures the surgeon cannot directly view the path of advancement of the shunt into the brain while advancing the shunt into the brain.

Instead, a magnetic resonance imaging scan or CT scan is performed to generate an image of the patient's brain, sometime prior to shunt placement. This image is subsequently displayed in the operating room during the shunt placement procedure, and the surgeon "eyeballs" correct placement of the shunt based upon the image previously generated by the scan. In other words, the surgeon advances the shunt into the patient's brain not by viewing a real-time image of the brain, but by periodically glancing at a still-life image of the brain that has been generated prior to surgery. Not surprisingly, accurate placement of a shunt under such conditions is not always performed optimally.

Accordingly, it is an object of the present invention to provide a device for positioning a shunt in a brain of a patient to relieve hydrocephalus. It is another object of the present invention to provide a device for presenting an image of the pathway of advancement of a shunt into the brain of a patient, during the placement procedure. It is a further object of the present invention to provide a device for positioning a shunt which is easy to use and cost-effective to manufacture.

SUMMARY OF THE INVENTION

A device for relieving hydrocephalus in the brain of a patient includes a shunt which has a distal end, and the distal end of the shunt is formed with an aperture. A tubular member is positionable within the shunt. The tubular member has a distal end abutting the distal end of the shunt, but not protruding past the aperture.

PATENT Consequently, the tubular member can be advanced into the brain to advance the shunt into the brain.

Also, an optical image fiber is positioned within the tubular member, and the optical image fiber has a distal end that protrudes beyond the distal end of the tubular member and the aperture of the shunt. Preferably, a video monitor is operably connected to the image fiber for presenting an image of the brain.

In one presently preferred embodiment, the shunt is a flexible catheter, and the aperture is a slit. In this embodiment, the tubular member is a stainless steel hypodermic tube (hypotube), and at least one optical illumination fiber is positioned in the hypotube adjacent the image fiber.

Moreover, an irrigating fluid passageway is established between the hypotube and the image fiber, and a source of irrigating fluid is in fluid communication with the irrigating fluid passageway. Further, a vacuum passageway is established between the hypotube and the image fiber, and a source of vacuum is in fluid communication with the vacuum passageway. Accordingly, the operating site within the brain can be irrigated and evacuated, to aid in generating a clear image of the operating site.

In another aspect of the present invention, a device is disclosed for positioning, in the brain of a patient, a flexible hollow shunt which has a closed distal end and an aperture formed in the distal end. The device includes a tube having a distal end and an outside diameter smaller than the inside diameter of the shunt and larger than the aperture. Also, the device has an optical image fiber positioned in the tube. The image fiber has a distal end which protrudes beyond the distal end of the tube, and the tube can be positioned in the shunt such that the distal end of the tube abuts the distal end of the shunt and the distal end of the image fiber protrudes beyond the aperture of the shunt.

In yet another aspect of the present invention, a method is disclosed for positioning a shunt in the brain of a patient. The shunt has a closed distal end formed with an aperture, and the method includes the steps of providing a hollow tube having a distal end, and positioning an optical image fiber in the tube. The image fiber has a distal end that protrudes beyond the distal end of the tube.

An image of the brain from the image fiber is displayed on a video monitor, and the tube is positioned inside the shunt with the distal end of the tube abutting the distal end of the shunt and the distal end of the image fiber protruding beyond the aperture. Then, the tube with shunt is advanced into the brain of the patient, while the surgeon views on the monitor the image of the brain generated by the image fiber.

In another preferred embodiment, a device for relieving hydrocephalus in the brain of a patient includes a ventricular catheter which has a distal end, and the distal end of the catheter is formed with a slit. A tubular member is positionable within the catheter, and the tubular member has a distal end abutting the distal end of the catheter.

Also, a light transmitting member, preferably an optical image fiber, is positioned within the tubular member, and the optical image fiber has a distal end that is positioned adjacent the distal end of the tubular member. The tubular member with catheter is advanced into the brain, and once the catheter has been positioned appropriately, the tubular member is pushed through the slit of the catheter to permit light from beyond the distal end of the catheter to enter the distal end of the light transmitting member.

In one presently preferred embodiment, the catheter is a flexible shunt. In this embodiment, the tubular member is a stainless steel hypodermic tube (hypotube), and at least one optical illumination fiber is positioned in the hypotube adjacent the image fiber.

In another aspect of the alternate embodiment of the present invention, a device is disclosed for positioning, in the brain of a patient, a flexible hollow shunt which has a closed distal end and an aperture formed in the distal end. The device includes a tube having a distal end and an outside diameter smaller than the inside diameter of the shunt and larger than the aperture. Also, the device has a light transmitting member, preferably an optical image fiber, positioned in the tube. The image fiber has a distal end juxtaposed with the distal end of the tube, and the tube can be positioned through the aperture of the shunt such that light from beyond the distal end of the shunt can enter the image fiber.

In yet another aspect of the present invention, a method is disclosed for positioning a shunt in the brain of a patient. The shunt has a closed distal end formed with an aperture, and the method includes the steps of providing a hollow tube having a distal end, and disposing an optical image fiber in the tube. The image fiber has a distal end that is positioned adjacent the distal end of the tube.

An image of the brain from the image fiber is displayed on a video monitor, and the tube is positioned inside the shunt with the distal end of the tube closely spaced from the distal end of the shunt. Then, the tube with shunt is advanced into the brain of the patient. Once the shunt has been properly positioned, the tube is advanced through the aperture of the shunt, and the surgeon views on the monitor the image of the brain generated by the image fiber.

The details of the present invention, both as to its construction and operation, can best be understood in reference to the accompanying drawings, in which like numerals refer to like parts, and which:

BRIEF DESCRIPTION OF THE DRAWINGS

FIG. 1 is a perspective view of the endoscope for shunt placement of the present invention, with portions broken away and with the associated auxiliary components shown in an exploded relationship, and the video monitor shown schematically;

FIG. 2 is a partial cross-sectional view of the endoscope for shunt placement of the present invention, as seen along the line 2—2 in FIG. 1;

FIG. 3 is a cross-sectional view of the endoscope for shunt placement of the present invention, as seen along the line 3—3 in FIG. 1, with the distal segment of a ventricular shunt catheter shown in operable engagement with the endoscope;

FIG. 4 is a cross-sectional view of the endoscope for shunt placement of the present invention, as seen along the line 4—4 in FIG. 1, with portions broken away;

FIG. 5 is a cross-sectional view of the endoscope for shunt placement of the present invention, as seen along the line 5—5 in FIG. 1;

FIG. 6 is a perspective view of the distal segment of an alternate embodiment of the present invention, with portions broken away and the handle removed for clarity;

FIG. 7 is a perspective view of an alternate embodiment of the present invention;

FIG. 8 is a cross-sectional view as seen along the line 8—8 in FIG. 7, with portions broken away;

FIG. 9A is a partial cross-sectional view as would be seen along the line 9—9 in FIG. 7, with the endoscope in operable engagement with a ventricular catheter in the advancing position; and FIG. 9B is a partial cross-sectional view as would be seen along the line 9—9 in FIG. 7, with the endoscope in operable engagement with a ventricular catheter in the viewing position.

DETAILED DESCRIPTION OF THE PREFERRED EMBODIMENT

Referring initially to FIG. 1, an endoscopic device for shunt placement is shown, generally designated 10. As shown, the endoscopic device 10 includes an endoscope 12 which is disposed within a tubular member, preferably an axially rigid stainless steel hollow hypodermic tube (hypotube) 14. In turn, the hypotube 14 is fixedly attached to a hard plastic or metal handle 16.

FIG. 1 shows that in the presently preferred embodiment, the handle 16 has a distally-tapered frusto-conical nose portion 18 and a proximal fitting mount 20, and the proximal fitting mount 20 is generally triangular in shape with two opposed parallel flat surfaces 22, 24. Also, the fitting mount 20 has a flat proximal end plug 26, and several fittings are connected to the proximal end plug 26.

More specifically, in cross-reference to FIGS. 1 and 2, a hollow, generally cylindrical image fiber hub 28 is positioned in a hub passageway 30 that is formed in the plug 26 of the handle 16. Preferably, the image fiber hub 28 is potted to the plug 26. A video coupler 32 can be engaged with the image fiber hub 28, and the coupler 32 can in turn be connected to a video transmission line 33 which is connected to a video camera with monitor 35 by means well-known in the art.

Further, a hollow, generally cylindrical illuminating cable connector 34 is positioned in a cable connector passageway 36 that is formed in the plug 26 of the handle 16. Preferably, the illuminating cable connector 34 is potted to the plug 26. A light transmission cable 38 can be engaged with the coupler 34, and the cable 38 can in turn be connected to a source of illuminating light (not shown) by means well-known in the art.

Additionally, a hollow, generally cylindrical irrigating fluid connector 40 is positioned in an irrigating fluid connector passageway 42 that is formed in the plug 26 of the handle 16. Preferably, the irrigating fluid connector 40 is configured as a female luer fitting, and is potted to the plug 26. A male luer fitting 44 with fluid line can be engaged with the connector 40, and the fluid line can in turn be connected to a source of irrigating fluid (not shown) by means well-known in the art.

Moreover, a hollow, generally cylindrical vacuum fitting 46 is positioned in a vacuum fitting passageway 48 that is formed in the plug 26 of the handle 16. Preferably, the vacuum fitting 46 is configured as a female luer fitting, and is potted to the plug 26. A male luer fitting 50 with fluid line can be engaged with the fitting 46, and the fluid line can in turn be connected to a source of vacuum (not shown) by means well-known in the art.

FIG. 2 best shows that an image fiber 52 is connected to the image fiber hub 28. Accordingly, the image fiber 52 is operably engaged with the video coupler 32. In one presently preferred embodiment, the image fiber 52 is a Sumitomo image fiber assembly that includes a bundle of optical fibers.

Also, an illuminating fiber bundle 54 is connected to the illuminating cable connector 34. Accordingly, the bundle 54 is operably engaged with the source of illuminating light. As shown in FIG. 2, the bundle 54 and image fiber 52 are juxtaposed in an optical fiber bundle to establish the endoscope 12.

Further, a thin wall, high strength irrigating fluid tube 56, preferably made of polyimide, is connected to the irrigating fluid connector 40, and the irrigating fluid tube 56 establishes an irrigating fluid passageway. The irrigating fluid tube 56 is operably engaged with the source of irrigating fluid. Similarly, a high-strength vacuum tube 58 is connected to the vacuum connector 50. The vacuum tube 58 establishes a vacuum passageway, and the vacuum passageway is operably engaged with the source of vacuum. Because the interior of the handle 16 is sealed, the vacuum tube 58 may be dispensed with.

Still referring to FIG. 2, the endoscope 12, irrigating fluid tube 56, and vacuum tube 58 extend into a proximal segment 60 of the hypotube 14. As shown, the hypotube 14 is held within the nose portion 18 of the handle 16, preferably by epoxy potting the hypotube 14 in the nose portion 18.

Now referring to FIGS. 3 and 4, the details of the hollow stainless steel hypotube 14 can be seen. As shown best in FIG. 3, the hypotube 14 has an outside diameter 62 of about fifty thousandths of an inch (0.050") and an inside diameter 64 of about forty-five thousandths of an inch (0.045"). The irrigating fluid tube 56, which is disposed within the hypotube 14, has an outside diameter 66 of about twelve thousandths of an inch (0.012") and an inside diameter 68 of about ten thousandths of an inch (0.010").

FIG. 3 further shows that the image fiber 52 has a diameter 70 of about eighteen thousandths of an inch (0.018"). It is to be understood in reference to FIGS. 3 and 4 that the image fiber 52 includes a suitable lens 72 (FIG. 4), e.g., a rod lens, which is attached to the distal end of the image fiber 52 by means well-known in the art for collecting light and transmitting the light back through the image fiber 52.

FIG. 3 also shows that the bundle 54 of optical illumination fibers includes a plurality of illumination fibers which are radially spaced from image fiber 52 and which are parallel to the image fiber 52. In the presently preferred embodiment, the bundle 54 includes six (6) optical illumination fibers, each having a diameter 74 of about ten thousandths of an inch (0.010").

Still referring to FIGS. 3 and 4, an epoxy material 76 is deposited within the hypotube 14 in the space between the irrigating fluid tube 56, image fiber 52, and bundle 54 of illuminating fibers by means well-known in the art. During the deposition of the epoxy material 76, a mandrill (not shown) is positioned within the hypotube 14, and when the epoxy 76 solidifies, the mandrill is removed to establish a vacuum channel 78.

As can be appreciated in cross-reference to FIGS. 1, 3, 4, and 5, the epoxy material 76 fills only a distal segment 80 (FIGS. 1 and 4) of the hypotube 14, and the vacuum channel 78 (FIGS. 3 and 4) is in fluid communication with an empty lumen 82 (FIGS. 4 and 5) that is established by the remainder of the hypotube 14. It is to be understood that the vacuum tube 58 (FIG. 1) is in turn in fluid communication with the lumen 82 of the hypotube 14.

Consequently, irrigating fluid (e.g., saline solution) can be directed through the irrigating fluid tube 56 to irrigate the site which is intended to be viewed during shunt placement. By irrigating the site, the field of view of the image fiber 52 is cleared. At the same time, debris and excess fluid can be evacuated from the viewed site through the vacuum channel 78, lumen 82, and vacuum tube 58. Preferably, the amount (i.e., mass flow rate) of fluid evacuated through the vacuum channel 78 is equal to the amount of irrigating fluid directed through the irrigating fluid tube 56. By properly establishing the inlet and outlet flow rates through the endoscopic device 10, and positioning the outlet of the device 10 at the appropriate elevation, intercranial pressure in the patient can be maintained at a predetermined pressure.

Referring now to FIG. 4, the operation of the device 10 can be seen. First, the hypotube 14 is advanced into a ventricular shunt catheter 84 having a distal segment 85 formed with a plurality of small holes 87 for draining fluid. Specifically, the hypotube 14 is advanced into the shunt 84 until a shoulder 86 which is formed by the distal end of the hypotube 14 abuts the closed distal end 88 of the shunt 84.

As shown in FIG. 4, the closed distal end 88 of the shunt 84 is formed with an aperture 90, and a distal segment 92 of the image fiber 52 protrudes through the aperture 90. In accordance with the present invention, the aperture 90 can be a slit and may have a circular cross-section, an oval cross-section, a rectangular cross-section, or another suitable configuration. If desired, an insert 91 having a distally-tapered slit 93 can be positioned in the aperture 90 for strength, and for guiding the shoulder 86 into contact with the insert 91.

In any case, the aperture 90 is sufficiently large to permit the distal segment 92 of the image fiber 52 to protrude through the aperture 90, but sufficiently small to prevent the shoulder 86 of the hypotube 14 from protruding through the aperture 90.

After the hypotube 14 has been advanced into the shunt 84 with the shoulder 86 abutting the distal end 88 of the shunt 84, the hypotube 14 with shunt 84 is advanced into the brain of a patient by manually pushing the device 10 toward the patient. As will be appreciated by the skilled artisan, the pushing force on the device 10 is transferred to the closed end 88 of the shunt 84 through the shoulder 86 of the hypotube 14.

As the shunt 84 is advanced into the patient, light from the intended path of advancement enters the image fiber 52 and is presented on the video monitor 35 (FIG. 1), which it will be recalled is operably engaged with the image fiber 52. The video monitor 35 is preferably positioned nearby the surgeon, so that the surgeon can view the path of advancement of the shunt 84 on the monitor 35 as he advances the shunt 84 into the patient.

Also, while the hypotube 14 with shunt 84 is advanced into the patient, irrigating fluid can be directed through the irrigating fluid tube 56 to irrigate the path of advancement. Stated differently, irrigating fluid can be directed through the irrigating fluid tube 56 to displace the CSF biological liquid which normally surrounds the spinal cord and brain, and which is ordinarily cloudy. Further, debris and excess fluid can be evacuated from the path of advancement through the vacuum channel 78. Thereby, a clear, unclouded view of the path of intended advancement of the shunt 84 can be displayed on the video monitor 35.

Now referring to FIG. 6, an alternate embodiment of the endoscopic device of the present invention is shown, generally designated 100. As shown, the device 100 does not include a hypotube, but instead has a scope body 102 made of a high modulus, high strength thermoplastic extrusion such as polyvinylchloride (PVC), nylon, polysulfone, or polycarbonate. As shown, the scope body 102 has a cylindrical proximal segment 104, a cylindrical distal segment 106, and a frusto-conical-shaped tapered segment 108. As shown, the segment 108 tapers inwardly from the proximal segment 104 to the distal segment 106. The proximal segment 104 is connected to a handle (not shown) similar to the handle 16, shown in FIG. 1, and preferably has an outer diameter 110 of about fifty thousandths of an inch (0.050").

FIG. 6 also shows that the device 100 includes an imaging segment 112. As shown, the imaging segment 112 includes an image fiber 114 and a plurality of illumination fibers 116. Moreover, the imaging segment 112 has an irrigation channel 118 and a vacuum channel 120. As further shown, an epoxy material 122 is deposited between the components of the imaging segment 112. A shoulder 124 is established by the distal end of the distal segment 106. The shoulder 124 abuts the distal end of a shunt catheter (not shown, but similar to the shunt 84 shown in FIG. 4), while the imaging segment 112 protrudes through an aperture formed in the shunt catheter, in the same manner as the shoulder 86 abuts the distal end 88 of the shunt catheter 84 in FIG. 4.

Now referring to FIGS. 7 and 8, a neuro endoscope is shown, generally designated 200. The endoscope 200 has a handle 202 which is similar to the handle 16 (FIG. 1). Specifically, the handle 202 has an image fiber hub 204, an irrigating fluid connector 206, and an illuminating fiber hub 208 which are in all essential respects identical to the hub 28, connector 40, and connector 34, respectively, shown in FIG. 1. In contrast to the handle 16, however, the handle 202 does not include a vacuum connector.

FIG. 8 best shows that a tubular member 210 extends into and through a distal end 212 of the handle 202, and is preferably potted thereto. The tubular member 210 preferably is a stainless steel hypotube. The member 210 holds an endoscope 211 (shown in FIGS. 9A and 9S) which is in all essential respects identical to the endoscope 12 shown in FIG. 1, except that the distal end of the endoscope 211 is flush with the open distal end of the hypotube 210. Also, depth bands 213 are etched on the outer surface of the hypotube 210, to provide a visual indication of the extent of the advancement of the hypotube 210 into a patient.

As intended by the present invention, the endoscope 211 includes a plurality of optical illumination fibers 214 and a light transmitting member, preferably a coherent optical image fiber 216. In an alternate embodiment, the light transmitting member can be a rigid rod lens, e.g., a Selfoc$^R$ lens. The illumination fibers 214 are operably connected to the illuminating fiber hub 208, while the image fiber 216 is operably connected to the image fiber hub 204. All of the fibers 214, 216 are disposed in the endoscope 211 in substantially the same manner as the fibers 52, 54 are disposed in the endoscope 12. It is to be understood that a video display apparatus (not shown) is operably engaged with the fiber hubs 204, 208.

Recall that the hypotube 14 included a vacuum channel 78 and an irrigating fluid tube 56. In contrast, the hypotube 210 includes two irrigating fluid channels (not shown) and no vacuum channel, to effect improved irrigation of the surgery site at low fluid pressures. Both irrigating fluid channels are connected to an inner irrigation tube (not shown) which is surrounded and supported by a first fluid tube 218, and the first fluid tube 218 is in turn connected to a second fluid tube 220 by means well-known the art. As shown best in FIG. 8, the second fluid tube 220 is attached to the irrigating fluid connector 206. Preferably, the first fluid tube 218 is a strain relief tube.

FIG. 8 best shows that the hypotube 210 has a proximal segment 222, and that a strain relief shrink tube 224 closely surrounds the proximal segment 222 to protect the image and illumination fibers 216, 214 and the first irrigating fluid tube 218. Also, a polyvinylchloride (PVC) protector tubing 226 surrounds and protects the illumination fibers 214. As shown, the PVC tubing 226 has a proximal terminus 227 spaced from the illuminating fiber hub 208.

Now referring to FIGS. 9A and 9B, the operation of the neuro endoscope 200 can be appreciated. A shunt, preferably a ventricular catheter 228 having a distal segment 229 formed with a plurality of small holes 231 for draining fluid, has a closed distal end 230, and a slit 232 is longitudinally formed through the distal end 230. The catheter 228 is positioned around a distal segment 233 of the hypotube 210, and, as shown in FIG. 9A, the distal end 230 of the catheter 228 is spaced from the distal end 234 of the hypotube 210. The skilled artisan will appreciate that a segment of the catheter 228 can be inwardly pinched or squeezed against the neuro endoscope 200 to hold the catheter 228 in the relationship shown in FIG. 9A.

With the catheter 228 positioned as shown in FIG. 9A (i.e., the advancement position), the neuro endoscope 200 with catheter 228 can be advanced into the brain of a patient. In the advancement position, the slit 232 is substantially closed, i.e., fluid cannot pass through the slit 232. Periodically, the distal end 234 of the hypotube 210 (and, hence, the distal end of the endoscope 211) can be selectively manually advanced through the slit 232 of the catheter 228 to the position shown in FIG. 9B (i.e., the viewing position) to collect light from beyond the distal end 230 of the catheter 228. In the viewing position, the slitted area of the catheter 228 closely surrounds the hypotube 210. When desired, the distal end 234 of the endoscope 211 can be retracted back into the catheter 228 to resume advancing the catheter 228 into the patient.

It will be appreciated that when the distal end 234 of the hypotube 210 is in the viewing position shown in FIG. 9B, an image of the portion of the brain which is immediately distal to the catheter 228 can be presented on the video monitor (not shown) which is operably connected to the image fiber hub 204 (FIGS. 7 and 8). The surgeon can accordingly view the pathway of intended advancement of the catheter 228 to aid the surgeon in properly positioning the catheter 228 within the brain of the patient.

While the particular endoscope for shunt placement as herein shown and described in detail is fully capable of attaining the above-described objects of the invention, it is to be understood that it is the presently preferred embodiment of the present invention and is thus representative of the subject matter which is broadly contemplated by the present invention, that the scope of the present invention fully encompasses other embodiments which may become obvious to those skilled in the art, and that the scope of the present invention is accordingly to be limited by nothing other than the appended claims.

What is claimed is:

1. A device for relieving hydrocephalus in the brain of a patient, comprising:

a ventricular shunt catheter having a distal end formed with a plurality of drain holes and an aperture;

a tubular member positionable within the ventricular shunt catheter, the tubular member having a distal end abutting the distal end of the ventricular shunt catheter; and an image fiber positioned within the tubular member, the image fiber having a distal end protruding beyond the distal end of the tubular member and the aperture of the ventricular shunt catheter.

2. The device of claim 1, wherein the the aperture is a slit.

3. The device of claim 2, wherein the tubular member is a hypotube.

4. The device of claim 3, further comprising at least one optical illumination fiber positioned adjacent the image fiber.

5. The device of claim 4, further comprising a video monitor operably connected to the image fiber for presenting an image of the brain.

6. The device of claim 5, wherein an irrigating fluid passageway is established between the hypotube and the image fiber.

7. The device of claim 6, wherein a vacuum passageway is established between the hypotube and the image fiber.

8. The device of claim 7, further comprising an insert positioned in the aperture of the ventricular shunt catheter, wherein the insert is formed with a slit.

9. A device, comprising:

a ventricular shunt catheter having a closed distal end and an aperture formed therein, the ventricular shunt catheter also having a plurality of drain holes formed therein, the catheter defining an inside diameter;

a tube having a distal end and defining an outside diameter smaller than the inside diameter of the ventricular shunt catheter and larger than the aperture; and an image fiber positioned in the tube, the image fiber having a distal end protruding beyond the distal end of the tube, wherein the tube can be positioned in the ventricular shunt catheter such that the distal end of the tube abuts the distal end of the ventricular shunt catheter and the distal end of the image fiber protrudes beyond the aperture of the ventricular shunt catheter.

10. The device of claim 9, wherein the aperture is a slit, and the tube is a hypotube.

11. The device of claim 10, further comprising at least one optical illumination fiber positioned adjacent the image fiber.

12. The device of claim 11, further comprising a video monitor operably connected to the image fiber for presenting an image of the brain.

13. The device of claim 12, wherein an irrigating fluid passageway is established between the hypotube and the image fiber, and a vacuum passageway is established between the hypotube and the image fiber.

14. A method for positioning a ventricular shunt catheter having a plurality of drain holes formed therein in the brain of a patient, wherein the ventricular shunt catheter has a closed distal end formed with an aperture, comprising the steps of:

(a) providing a hollow tube having a distal end;

(b) positioning an image fiber in the tube, the image fiber having a distal end protruding beyond the distal end of the tube;

(c) connecting a video monitor to the image fiber for displaying an image of the patient;

(d) positioning the tube inside the ventricular shunt catheter with the distal end of the tube abutting the distal end of the ventricular shunt catheter and the distal end of the image fiber protruding beyond the aperture; and (e) advancing the tube with the ventricular shunt catheter into the brain of the patient.

15. The method of claim 14, further comprising the step of establishing a fluid passageway between the tube and the image fiber, and directing irrigating fluid through the fluid passageway.

16. The method of claim 14, further comprising the step of establishing a vacuum passageway between the tube and the image fiber, and establishing a vacuum in the vacuum passageway.

* * * * *